(12) United States Patent
Ionkin et al.

(10) Patent No.: US 7,683,149 B2
(45) Date of Patent: Mar. 23, 2010

(54) CATALYSTS FOR OLEFIN POLYMERIZATION OR OLIGOMERIZATION

(75) Inventors: Alex S. Ionkin, Kennett Square, PA (US); Lynda Kaye Johnson, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 12/218,030

(22) Filed: Jul. 10, 2008

(65) Prior Publication Data

US 2008/0287621 A1 Nov. 20, 2008

Related U.S. Application Data

(62) Division of application No. 11/177,791, filed on Jul. 8, 2005, now Pat. No. 7,442,819.

(51) Int. Cl.
*C07F 15/02* (2006.01)
*C07F 15/04* (2006.01)

(52) U.S. Cl. .................. 526/171; 502/155; 502/167; 526/352; 526/172; 556/32

(58) Field of Classification Search ................ 502/155, 502/167; 526/171, 172, 352; 556/32
See application file for complete search history.

(56) References Cited

U.S. PATENT DOCUMENTS

| | | | |
|---|---|---|---|
| 3,781,291 | A | 12/1973 | Sulzbach et al. |
| 5,866,663 | A | 2/1999 | Brookhart et al. |
| 5,955,555 | A | 9/1999 | Bennett et al. |
| 6,063,881 | A | 5/2000 | Bennett et al. |
| 6,103,946 | A | 8/2000 | Brookhart et al. |
| 6,184,171 | B1 | 2/2001 | Shih et al. |
| 6,214,761 | B1 | 4/2001 | Bennett et al. |
| 6,252,002 | B1 | 6/2001 | Yamada et al. |
| 6,297,338 | B1 | 10/2001 | Cotts et al. |
| 6,313,061 | B1 | 11/2001 | Denton et al. |
| 6,399,535 | B1 | 6/2002 | Shih et al. |
| 6,403,521 | B1 * | 6/2002 | Ishii et al. ............ 502/150 |
| 6,407,188 | B1 | 6/2002 | Guan et al. |
| 6,451,939 | B1 | 9/2002 | Britovsek et al. |
| 6,455,660 | B1 | 9/2002 | Clutton et al. |
| 6,458,739 | B1 | 10/2002 | Kimberley et al. |
| 6,472,341 | B1 | 10/2002 | Kimberley et al. |
| 6,534,691 | B2 | 3/2003 | Culver et al. |
| 6,545,108 | B1 | 4/2003 | Moody et al. |
| 6,555,631 | B1 | 4/2003 | Wang et al. |
| 6,555,723 | B2 | 4/2003 | Schiffino et al. |
| 6,559,091 | B1 | 5/2003 | Moody et al. |
| 6,579,832 | B2 | 6/2003 | Jimenez et al. |
| 6,586,541 | B2 | 7/2003 | Citron et al. |
| 6,610,805 | B1 * | 8/2003 | Guram et al. ............ 526/172 |
| 6,620,895 | B1 | 9/2003 | Cotts et al. |
| 6,620,897 | B1 | 9/2003 | Smillie et al. |
| 6,657,026 | B1 | 12/2003 | Kimberley et al. |
| 6,683,187 | B2 | 1/2004 | De Boer et al. |
| 6,710,006 | B2 | 3/2004 | De Boer et al. |

FOREIGN PATENT DOCUMENTS

| | | |
|---|---|---|
| WO | WO 99/12981 | 3/1999 |
| WO | WO 99/46302 | 9/1999 |
| WO | WO 99/46303 | 9/1999 |
| WO | WO 99/46304 | 9/1999 |
| WO | WO 00/24788 | 5/2000 |
| WO | WO 00/32641 | 6/2000 |
| WO | WO 00/50470 | 8/2000 |
| WO | WO 00/69869 | 11/2000 |
| WO | WO 00/69923 | 11/2000 |
| WO | WO 00/73249 A1 | 12/2000 |
| WO | WO 02/079276 A2 | 10/2002 |
| WO | WO 02/083751 A1 | 10/2002 |
| WO | WO 03/059511 A1 | 7/2003 |
| WO | WO 2004/026795 A2 | 4/2004 |

OTHER PUBLICATIONS

Greon et al., Eur. J. Inorg. Chem. 1998, pp. 1129-1143.*
U.S. Appl. No. 60/505,906, filed Sep. 25, 2003, Spence et al.
Johannes H. Groen et al., Insertion Reactions Into Palladium-Carbon Bonds of Complexes Containing Terdentate Nitrogen Ligands: Experimental And Ab Initio MO Studies, European Journal Of Inorganic Chemistry 1998, vol. 8, pp. 1129-1143.
Alison M. A. Bennett et al., Novel, Highly Active Iron and Cobalt Catalysts For Olefin Polymerization, Chemtech, 1999, vol. 29, pp. 24-28.
Wolfgang Beck et al., metal Complexes Of Weakly Coordinating Anions. Precursors of Strong Cationic Organometallic lewis Acids, American Chemical Society, 1988, vol. 88, pp. 1405-1421.
Steven H. Strauss et al., The Search For Larger And More Weakly Coordinating Anions, American Chemical Society, 1993, vol. 93, pp. 927-942.
Brooke L. Small et al.., Highly Active Iron And Cobalt Catalysts For The Polymerization Of Ethylene, American Chemical Society, 1998, vol. 120, pp. 4049-4050.
R.P. Thummel et al., Polyaza Cavilty Shaped Molecules. 4. Annelated Derivatives Of 2,2':6',2"-Terpyridine,1985, vol. 50, pp. 2407-2412.

* cited by examiner

*Primary Examiner*—Robert D. Harlan
(74) *Attorney, Agent, or Firm*—Barry D. Cash

(57) ABSTRACT

Novel iron and cobalt complexes of certain novel tricyclic ligands containing a "pyridine" ring and substituted with two imino groups are polymerization and/or oligomerization catalysts for olefins, especially ethylene. Depending on the exact structure of the ligand, and polymerization process conditions, products ranging from α-olefins to high polymers may be produced. The polymers, especially polyethylenes, are useful for films and as molding resins.

10 Claims, No Drawings

CATALYSTS FOR OLEFIN POLYMERIZATION OR OLIGOMERIZATION

FIELD OF THE INVENTION

Iron and cobalt complexes of certain tricyclic ligands containing a "pyridine" ring and substituted with two imino groups are polymerization and/or oligomerization catalysts for olefins, especially ethylene.

TECHNICAL BACKGROUND

Polyolefins are ubiquitous products in modern society, billions of kilograms being produced yearly. There has been a continuing interest in catalysts that can produce such polymers more cheaply and/or produce polymers with different structures and improved desirable properties. In the last decade or so, it has been found that certain late transition metal complexes can polymerize various olefins, often to form polymers which are difficult or impossible to obtain using other olefin polymerization catalysts.

Among these late transition metal catalysts have been iron and cobalt complexes of diimines of 2,6-pyridinedicarboxaldehydes and 2,6-diacylpyridines, which are especially useful for polymerization or oligomerization of ethylene, see for instance U.S. Pat. Nos. 5,955,555 and 6,103,946 and 6,545,108. It has now been discovered that iron and cobalt complexes of certain tricyclic ligands containing a "pyridine ring" and substituted with two imino groups are catalysts for the polymerization and/or oligomerization of olefins, especially ethylene.

SUMMARY OF THE INVENTION

This invention concerns a process for the polymerization or oligomerization of olefins, comprising, contacting one or more olefins of the formula $R^1CH{=}CH_2$ (I), with an iron or cobalt complex of a diimine of a diketone of the formula

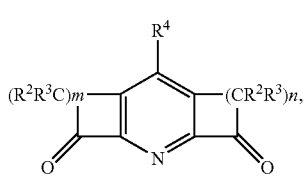

(II)

wherein:
$R^1$ is hydrogen or n-alkyl;
m and n are each independently an integer of 1 to 5;
each $R^2$ and $R^3$ is independently hydrogen, hydrocarbyl, substituted hydrocarbyl or a functional group; and
$R^4$ is hydrogen, hydrocarbyl, substituted hydrocarbyl, or a functional group.

Also disclosed herein is a compound of the formula

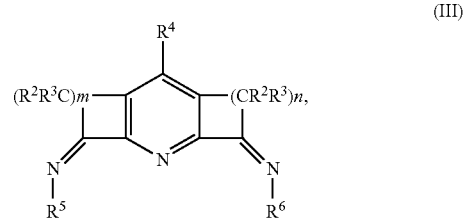

(III)

wherein:
m and n are each independently an integer of 1 to 5;
each $R^2$ and $R^3$ is independently hydrogen, hydrocarbyl, substituted hydrocarbyl, or a functional group;
$R^4$ is hydrogen, hydrocarbyl, substituted hydrocarbyl, or a functional group; and
$R^5$ and $R^6$ are each independently hydrocarbyl or substituted hydrocarbyl.

This invention also concerns an iron or cobalt complex of a ligand of the formula

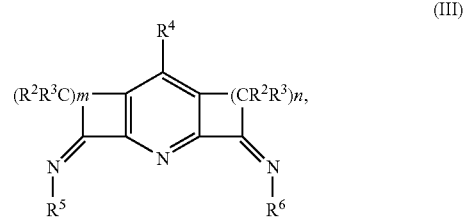

(III)

wherein:
m and n are each independently an integer of 2 to 5;
each $R^2$ and $R^3$ is independently hydrogen, hydrocarbyl, substituted hydrocarbyl, or a functional group;
$R^4$ is hydrogen, hydrocarbyl, substituted hydrocarbyl, or a functional group; and
$R^5$ and $R^6$ are each independently hydrocarbyl or substituted hydrocarbyl.

DETAILS OF THE INVENTION

Herein certain terms are used, and many of them are defined below.

A "hydrocarbyl group" is a univalent group containing only carbon and hydrogen. As examples of hydrocarbyls may be mentioned unsubstituted alkyls, cycloalkyls and aryls. If not otherwise stated, it is preferred that hydrocarbyl groups (and alkyl groups) herein contain 1 to about 30 carbon atoms.

By "substituted hydrocarbyl" herein is meant a hydrocarbyl group that contains one or more substituent groups that are inert under the process conditions to which the compound containing these groups is subjected (e.g., an inert functional group, see below). The substituent groups also do not substantially detrimentally interfere with the polymerization process or operation of the polymerization catalyst system. If not otherwise stated, it is preferred that (substituted) hydrocarbyl groups herein contain 1 to about 30 carbon atoms. Included in the meaning of "substituted" are rings containing one or more heteroatoms, such as nitrogen, oxygen and/or sulfur, and the free valence of the substituted hydrocarbyl may be to the heteroatom. In a substituted hydrocarbyl, all of the hydrogens may be substituted, as in trifluoromethyl.

By "(inert) functional group" herein is meant a group, other than hydrocarbyl or substituted hydrocarbyl, which is inert under the process conditions to which the compound containing the group is subjected. The functional groups also do not substantially deleteriously interfere with any process described herein that the compound in which they are present may take part in. Examples of functional groups include halo (fluoro, chloro, bromo and iodo), and ether such as —$OR^{50}$ wherein $R^{50}$ is hydrocarbyl or substituted hydrocarbyl. In cases in which the functional group may be near a transition metal atom, the functional group alone should not coordinate to the metal atom more strongly than the groups in those compounds that are shown as coordinating to the metal atom, that is they should not displace the desired coordinating group.

By a "cocatalyst" or a "catalyst activator" is meant one or more compounds that react with a transition metal compound to form an activated catalyst species. One such catalyst activator is an "alkylaluminum compound" which, herein, means a compound in which at least one alkyl group is bound to an aluminum atom. Other groups such as, for example, alkoxide, hydride, an oxygen atom bridging two aluminum atoms, and halogen may also be bound to aluminum atoms in the compound.

By a "linear α-olefin product" is meant a composition predominantly comprising a compound or mixture of compounds of the formula $H(CH_2CH_2)_qCH=CH_2$ wherein q is an integer of 1 to about 18. In most cases, the linear α-olefin product of the present process will be a mixture of compounds having differing values of q of from 1 to 18, with a minor amount of compounds having q values of more than 18. Preferably less than 50 weight percent, and more preferably less than 20 weight percent, of the product will have q values over 18. The product may further contain small amounts (preferably less than 30 weight percent, more preferably less than 10 weight percent, and especially preferably less than 2 weight percent) of other types of compounds such as alkanes, branched alkenes, dienes and/or internal olefins.

By a "primary carbon group" herein is meant a group of the formula —$CH_2$—, wherein the free valence—is to any other atom, and the bond represented by the solid line is to a ring atom of a substituted aryl to which the primary carbon group is attached. Thus the free valence—may be bonded to a hydrogen atom, a halogen atom, a carbon atom, an oxygen atom, a sulfur atom, etc. In other words, the free valence— may be to hydrogen, hydrocarbyl, substituted hydrocarbyl or a functional group. Examples of primary carbon groups include —$CH_3$, —$CH_2CH(CH_3)_2$, —$CH_2Cl$, —$CH_2C_6H_5$, —$OCH_3$ and —$CH_2OCH_3$.

By a "secondary carbon group" is meant the group

wherein the bond represented by the solid line is to a ring atom of a substituted aryl to which the secondary carbon group is attached, and both free bonds represented by the dashed lines are to an atom or atoms other than hydrogen. These atoms or groups may be the same or different. In other words the free valences represented by the dashed lines may be hydrocarbyl, substituted hydrocarbyl or inert functional groups. Examples of secondary carbon groups include —$CH(CH_3)_2$, —$CHCl_2$, —$CH(C_6H_5)_2$, cyclohexyl, —$CH(CH_3)OCH_3$, and —$CH=CCH_3$.

By a "tertiary carbon group" is meant a group of the formula

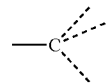

wherein the bond represented by the solid line is to a ring atom of a substituted aryl to which the tertiary carbon group is attached, and the three free bonds represented by the dashed lines are to an atom or atoms other than hydrogen. In other words, the bonds represented by the dashed lines are to hydrocarbyl, substituted hydrocarbyl or inert functional groups. Examples of tertiary carbon groups include —$C(CH_3)_3$, —$C(C_6H_5)_3$, —$CCl_3$, —$CF_3$, —$C(CH_3)_2OCH_3$, —$C\equiv CH$, —$C(CH_3)_2CH=CH_2$, aryl and substituted aryl such as phenyl, and 1-adamantyl.

By relatively noncoordinating (or weakly coordinating) anions are meant those anions as are generally referred to in the art in this manner, and the coordinating ability of such anions is known and has been discussed in the literature, see for instance W. Beck., et al., Chem. Rev., vol. 88 p. 1405-1421 (1988), and S. H. Stares, Chem. Rev., vol. 93, p. 927-942 (1993), both of which are hereby included by reference. Among such anions are those formed from the aluminum compounds in the immediately preceding paragraph and $X^-$ including $R^9_3AlX^-$, $R^9_2AlClX^-$, $R^9AlCl_2X^-$, and "$R^9AlOX^-$", wherein $R^9$ is alkyl. Other useful noncoordinating anions include $BAF^-$ {BAF=tetrakis[3,5-bis(trifluoromethyl)phenyl]borate}, $SbF_6^-$, $PF_6^-$, and $BF_4^-$, trifluoromethanesulfonate By a "monoanionic ligand" is meant a ligand with one negative, charge.

By a "neutral ligand" is meant a ligand that is not charged.

"Alkyl group" and "substituted alkyl group" have their usual meaning (see above for substituted under substituted hydrocarbyl). Unless otherwise stated, alkyl groups and substituted alkyl groups preferably have 1 to about 30 carbon atoms.

By "aryl" is meant a monovalent aromatic group in which the free valence is to the carbon atom of an aromatic ring. An aryl may have one or more aromatic rings, which may be fused, connected by single bonds or other groups.

By "substituted aryl" is meant a monovalent aromatic group substituted as set forth in the above definition of "substituted hydrocarbyl". Similar to an aryl, a substituted aryl may have one or more aromatic rings, which may be fused, connected by single bonds or other groups; however, when the substituted aryl has a heteroaromatic ring, the free valence in the substituted aryl group can be to a heteroatom (such as nitrogen) of the heteroaromatic ring instead of a carbon.

By "polymerization" is meant herein, in its broadest context, to include dimerization, oligomerization and polymerization (both homopolymerization and copolymerization).

By "polymerization conditions" herein is meant conditions for causing olefin "polymerization" with catalysts described herein. Such conditions may include temperature, pressure, suspending media, polymerization method such as gas phase, liquid phase, continuous, batch, and the like. Also included may be cocatalysts.

The iron or cobalt complexes of (III) may be used to polymerize and/or oligomerize olefins. Whether the olefin is polymerized or oligomerized [in other words what is the (average) molecular weight of the resulting product] will depend on many factors, including the structure of the complex, polymerization conditions, which olefin is being polymerized, etc.

In (II) or (III), and their iron and cobalt complexes it is preferred that:
  every $R^2$ and $R^3$ is hydrogen; and/or
  m is equal to n; and/or
  m and n are 2 or 3; and/or
  $R^4$ is hydrogen; and/or
  the complex is an iron complex.

In (II) and (III) the structures of $R^5$ and $R^6$ are particularly important in determining the type of product by a polymerization, that is what the molecular weight of the "polymer" produced is. Generally speaking the more sterically "demanding" $R^5$ and $R^6$ are, the higher the molecular weight of the polymer produced. Thus in order to produce polymers, over all, the ligand (II) should create (have) sufficient steric hindrance about the transition metal atom in the complex (II) so that polymerization (in it broadest sense) takes place. For a discussion of steric hindrance with other tridentate ligands, see for instance B. L. Small, et al., J. Am. Chem. Soc., vol. 120, p. 4049-4050 (1998) and A. M. A. Bennett, Chemtech, vol. 29(7), p. 24-28 (1999), both of which are hereby included by reference.

Preferably $R^5$ and $R^6$ are each independently aryl or substituted aryl.

In one preferred form $R^5$ is $$\begin{array}{c} R^{12} \quad\quad R^8 \\ \\ R^{11} \quad\quad R^9 \\ R^{10} \end{array} \quad (IV)$$

and $R^6$ is $$\begin{array}{c} R^{17} \quad\quad R^{13} \\ \\ R^{16} \quad\quad R^{14} \\ R^{15} \end{array} \quad (V)$$

wherein:
  $R^8$, $R^{12}$, $R^{13}$ and $R^{17}$ are each independently hydrocarbyl, substituted hydrocarbyl or an inert functional group;
  $R^9$, $R^{10}$, $R^{11}$, $R^{14}$, $R^{15}$ and $R^{16}$ are each independently hydrogen, hydrocarbyl, substituted hydrocarbyl or an inert functional group;
  and provided that any two of $R^8$, $R^9$, $R^{10}$, $R^{11}$, $R^{12}$, $R^{13}$, $R^{14}$, $R^{15}$, $R^{16}$ and $R^{17}$ that are vicinal to one another, taken together may form a ring.

In (IV) and (V), it is preferred that:
  $R^9$, $R^{10}$, $R^{11}$, $R^{14}$, $R^{15}$ and $R^{16}$ are each independently hydrogen, halogen, or an alkyl containing 1 to 6 carbon atoms, and more preferably that each of these is hydrogen; and/or
  $R^{10}$ and $R^{15}$ are methyl, phenyl or substituted phenyl (such as an alkyl substituted phenyl); and/or
  $R^8$, $R^{12}$, $R^{13}$ and $R^{17}$ are each independently halogen, phenyl, substituted phenyl or an alkyl containing 1 to 6 carbon atoms, more preferably that each is independently phenyl, substituted phenyl (e.g., an alkyl substituted phenyl such as p-t-butylphenyl) or an alkyl containing 1-6 carbon atoms (such as i-propyl or t-butyl) (although it is not preferred when both $R^8$ and $R^{12}$, or both $R^{13}$ and $R^{17}$, are t-butyl in the same compound).

Specific preferred compounds are (in combination with any of the variants for $R^2$, $R^3$, and $R^4$ mentioned above) where $R^5$ and $R^6$ are, respectively, (IV) and (V), and:
  $R^9$, $R^{11}$, $R^{14}$ and $R^{16}$ are hydrogen, and $R^8$, $R^{10}$, $R^{12}$, $R^{13}$, $R^{15}$ and $R^{17}$ are methyl;
  $R^9$, $R^{10}$, $R^{11}$, $R^{14}$, $R^{15}$ and $R^{16}$ are hydrogen, $R^8$ and $R^{13}$ are chloro, and $R^{12}$ and $R^{17}$ are methyl;
  $R^9$, $R^{10}$, $R^{11}$, $R^{14}$, $R^{15}$, $R^{16}$ and $R^{17}$ are hydrogen, and $R^8$ and $R^{13}$ are phenyl;
  $R^9$, $R^{10}$, $R^{11}$, $R^{14}$, $R^{15}$, $R^{16}$ and $R^{17}$ are hydrogen, and $R^8$ and $R^{13}$ are p-t-butylphenyl;
  $R^9$, $R^{10}$, $R^{11}$, $R^{14}$, $R^{15}$ and $R^{16}$ are hydrogen, and $R^8$, $R^{12}$, $R^{13}$ and $R^{17}$ are phenyl;
  $R^9$, $R^{10}$, $R^{11}$, $R^{14}$, $R^{15}$ and $R^{16}$ are hydrogen, and $R^8$, $R^2$, $R^{13}$ and $R^{17}$ are p-t-butylphenyl;
  $R^9$, $R^{10}$, $R^{11}$, $R^{14}$, $R^{15}$ and $R^{16}$ are hydrogen, and $R^8$ and $R^{13}$ are phenyl, and $R^{12}$ and $R^{17}$ are halo;
  $R^9$, $R^{10}$, $R^{11}$, $R^{14}$, $R^{15}$ and $R^{16}$ are hydrogen, and $R^8$ and $R^{13}$ are p-t-butylphenyl, and $R^{12}$ and $R^{17}$ are halo;
  $R^9$, $R^{10}$, $R^{11}$, $R^{14}$, $R^{15}$ and $R^{16}$ are hydrogen, and $R^8$, $R^{12}$, $R^{13}$ and $R^{17}$ are i-propyl; and
  $R^9$, $R^{10}$, $R^{11}$, $R^{12}$, $R^{14}$, $R^{15}$, $R^{16}$ and $R^{17}$ are hydrogen, and $R^8$ and $R^{13}$ are t-butyl.

In another preferred variant of (II), $R^5$ and $R^6$ are each independently a substituted 1-pyrroyl. More preferably in this instance, $R^5$ and $R^6$ are, respectively $$\begin{array}{c} R^{20} \quad R^{19} \\ C=C \\ R^{21}-C \quad C-R^{18} \\ N \\ | \end{array} \quad \text{and} \quad (VI)$$

$$\begin{array}{c} R^{24} \quad R^{23} \\ C=C \\ R^{25}-C \quad C-R^{22} \\ N \\ | \end{array}, \quad (VII)$$

wherein:
  $R^{18}$ and $R^{21}$ correspond to the definitions of, and preferences for, $R^8$ and $R^{12}$ in (IV);
  $R^{22}$ and $R^{25}$ correspond to the definitions of, and preferences for, $R^{13}$ and $R^{17}$ in (V);
  $R^{19}$ and $R^{20}$ correspond to the definitions of, and preferences for, $R^9$ and $R^{11}$ in (IV); and
  $R^{23}$ and $R^{24}$ correspond to the definitions of, and preferences for, $R^{14}$ and $R^{16}$ in (V).

In "polymerizations" in which a dimer or oligomer, preferably an LAO, is produced, $R^5$ and $R^6$ are preferably each independently a substituted aryl having a first ring atom bound to the imino nitrogen, provided that:

in $R^5$, a second ring atom adjacent to said first ring atom is bound to a halogen, a primary carbon group, a secondary carbon group or a tertiary carbon group; and further provided that:

in $R^5$, when said second ring atom is bound to a halogen or a primary carbon group, none, one or two of the other ring atoms in $R^5$ and $R^6$ adjacent to said first ring atom are bound to a halogen or a primary carbon group, with the remainder of the ring atoms adjacent to said first ring atom being bound to a hydrogen atom; or in $R^5$, when said second ring atom is bound to a secondary carbon group, none, one or two of the other ring atoms in $R^5$ and $R^6$ adjacent to said first ring atom are bound to a halogen, a primary carbon group or a secondary carbon group, with the remainder of the ring atoms adjacent to said first ring atom being bound to a hydrogen atom; or in $R^5$, when said second ring atom is bound to a tertiary carbon group, none or one of the other ring atoms in $R^5$ and $R^6$ adjacent to said first ring atom are bound to a tertiary carbon group, with the remainder of the ring atoms adjacent to said first ring atom being bound to a hydrogen atom;

By a "first ring atom in $R^5$ and $R^6$ bound to an imino nitrogen atom" is meant the ring atom in these groups bound to an imino nitrogen shown in (II), for example

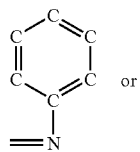
(VIII)

or

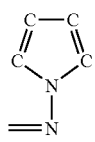
(IX)

the atoms shown in the 1-position in the rings in (VIII) and (IX) are the first ring atoms bound to an imino carbon atom (other groups which may be substituted on the aryl groups are not shown). Ring atoms adjacent to the first ring atoms are shown, for example, in (X) and (XI), where the open valencies to these adjacent atoms are shown by dashed lines [the 2,6-positions in (X) and the 2,5-positions in (XI)].

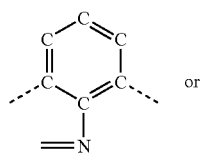
(X)

or

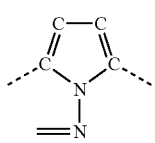
(XI)

In preferred dimerization/oligomerization embodiments, $R^5$ is

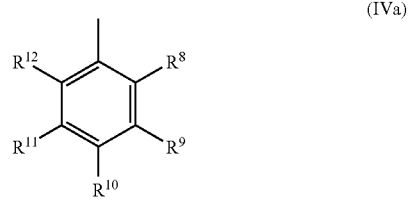
(IVa)

and $R^6$ is

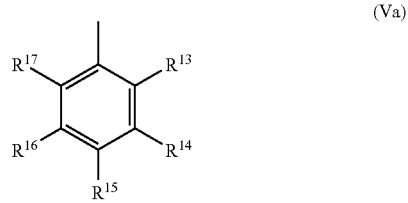
(Va)

wherein:

$R^8$ is a halogen, a primary carbon group, a secondary carbon group or a tertiary carbon group; and $R^9$, $R^{10}$, $R^{11}$, $R^{14}$, $R^{15}$, $R^{16}$ and $R^{17}$ are each independently hydrogen, hydrocarbyl, substituted hydrocarbyl or a functional group; provided that:

when $R^8$ is a halogen or primary carbon group none, one or two of $R^{12}$, $R^{13}$ and $R^{17}$ are a halogen or a primary carbon group, with the remainder of $R^{12}$, $R^{13}$ and $R^{17}$ being hydrogen; or when $R^8$ is a secondary carbon group, none or one of $R^{12}$, $R^{13}$ and $R^{17}$ is a halogen, a primary carbon group or a secondary carbon group, with the remainder of $R^{12}$, $R^{13}$ and $R^{17}$ being hydrogen; or when $R^8$ is a tertiary carbon group, none or one of $R^{12}$, $R^{13}$ and $R^{17}$ is tertiary carbon group, with the remainder of $R^2$, $R^{13}$ and $R^{17}$ being hydrogen;

and further provided that any two of $R^8$, $R^9$, $R^{10}$, $R^{11}$, $R^{12}$, $R^{13}$, $R^{14}$, $R^{15}$, $R^{16}$ and $R^{17}$ vicinal to one another, taken together may form a ring.

In the above formulas (IVa) and (Va), $R^8$ corresponds to the second ring atom adjacent to the first ring atom bound to the imino nitrogen, and $R^{12}$, $R^{13}$ and $R^{17}$ correspond to the other ring atoms adjacent to the first ring atom.

In compounds (II) or (III) containing (IVa) and (Va), it is particularly preferred that:

if $R^8$ is a primary carbon group, $R^{13}$ is a primary carbon group, and $R^{12}$ and $R^{17}$ are hydrogen; or if $R^8$ is a secondary carbon group, $R^{13}$ is a primary carbon group or a secondary carbon group, more preferably a secondary carbon group, and $R^{12}$ and $R^{17}$ are hydrogen; or if $R^8$ is a tertiary carbon group (more preferably a trihalo tertiary carbon group such as a trihalomethyl), $R^{13}$ is a tertiary carbon group (more preferably a trihalotertiary group such as a trihalomethyl), and $R^{12}$ and $R^{17}$ are hydrogen; or if $R^8$ is a halogen, $R^{13}$ is a halogen, and $R^{12}$ and $R^{17}$ are hydrogen.

In all specific preferred compounds (II) or (III) in which (IVa) and (Va) appear, it is preferred that $R^1$, $R^2$ and $R^3$ are hydrogen. It is further preferred that:

$R^9$, $R^{10}$, $R^{11}$, $R^{12}$, $R^{14}$, $R^{15}$, $R^{16}$ and $R^{17}$ are all hydrogen; $R^{13}$ is methyl; and $R^8$ is a primary carbon group, more preferably methyl; or $R^9$, $R^{10}$, $R^{11}$, $R^{12}$, $R^{14}$, $R^{15}$, $R^{16}$ and $R^{17}$ are all hydrogen; $R^{13}$ is ethyl; and $R^8$ is a primary carbon group, more preferably ethyl; or $R^9$, $R^{10}$, $R^{11}$, $R^{12}$, $R^{14}$, $R^{15}$, $R^{16}$ and $R^{17}$ are all hydrogen; $R^{13}$ isopropyl; and $R^8$ is a primary carbon group, more preferably methyl; or $R^9$, $R^{10}$, $R^{11}$, $R^{12}$, $R^{14}$, $R^{15}$, $R^{16}$ and $R^{17}$ are all hydrogen; $R^{13}$ is n-propyl; and $R^8$ is a primary carbon group, more preferably n-propyl; or $R^9$, $R^{10}$, $R^{11}$, $R^{12}$, $R^{14}$, $R^{15}$, $R^{16}$ and $R^{17}$ are all hydrogen; $R^{13}$ is chloro; and $R^8$ is a halogen, more preferably chloro; or $R^9$, $R^{10}$, $R^{11}$, $R^{12}$, $R^{14}$, $R^{15}$, $R^{16}$ and $R^{17}$ are all hydrogen; $R^{13}$ is trihalomethyl, more preferably trifluoromethyl; and $R^8$ is a trihalomethyl, more preferably trifluoromethyl.

In another preferred embodiment of (II) or (III), $R^5$ and $R^6$ are, respectively

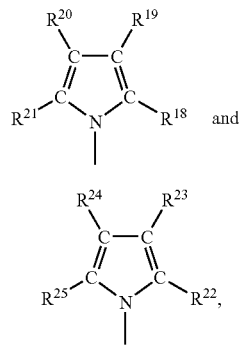

(VIIIa)

and (IXa)

wherein:

$R^{18}$ corresponds to the definitions of, and preferences for, $R^8$ (IVa);

$R^{19}$, $R^{20}$ and $R^{21}$ correspond respectively to the definitions of, and preferences for, $R^9$, $R^{10}$ and $R^{12}$ in (IVa); and $R^{22}$, $R^{23}$, $R^{24}$ and $R^{25}$ correspond respectively to the definitions of, and preferences for, $R^{13}$, $R^{14}$, $R^{16}$ and $R^{17}$ in (Va).

In the above formulas (VIIIa) and (IXa), $R^{18}$ corresponds to the second ring atom adjacent to the first ring atom bound to the imino nitrogen, and $R^{21}$, $R^{22}$ and $R^{25}$ correspond to the other ring atoms adjacent to the first ring atom.

Other useful groups for $R^5$ and $R^6$ are the same groups attached to imino group nitrogen atoms in tricyclic ligands and transition metal complexes described in Useful forms of complexes of (II) include those of the following formulas:

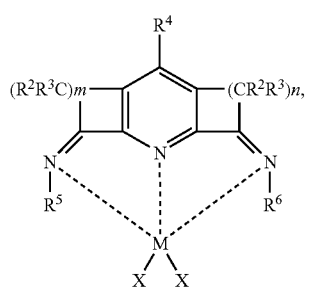

(XIII)

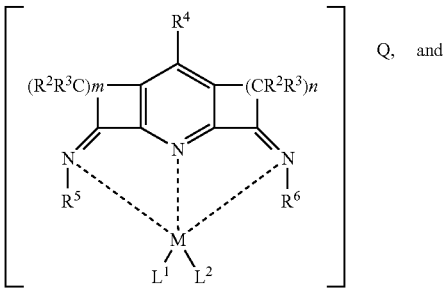

(XIV)

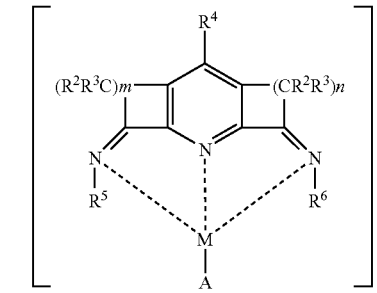

(XV)

wherein:
m and n are each independently an integer of 1 to 5;
each $R^2$ and $R^3$ is independently hydrogen, hydrocarbyl, substituted hydrocarbyl or a functional group; and
$R^4$ is hydrogen, hydrocarbyl substituted hydrocarbyl or a functional group;
M is Fe or Co;
each X is independently a monoanion;
A is a π-allyl or π-benzyl group;
$L^1$ is a neutral monodentate ligand which may be displaced by said olefin or an open coordination site, and $L^2$ is a monoanionic monodentate ligand which preferably can add to an olefin, or $L^1$ and $L^2$ taken together are a monoanionic bidentate ligand, provided that said monoanionic monodentate ligand or said monoanionic bidentate ligand may add to said olefin; and
Q is a relatively noncoordinating anion.

Preferably each X is independently halide or carboxylate, more preferably both of X are chloride or bromide.

When A is present, in effect $L^1$ and $L^2$ taken together are A. (XIII) may be used as a starting material for forming an active polymerization complex. For example (XIII) may be reacted with (a) a first compound W, which is a neutral Lewis acid capable of abstracting $X^-$ and alkyl group or a hydride group from M to form $WX^-$, $(WR^{40})^-$ or $WH^-$, wherein $R^{40}$ is alkyl, and which is also capable of transferring an alkyl group or a hydride to M, provided that $WX^-$ is a weakly coordinating anion; or (b) a combination of second compound which is capable of transferring an alkyl or hydride group to M and a third compound which is a neutral Lewis acid which is capable of abstracting $X^-$, a hydride or an alkyl group from M to form a weakly coordinating anion.

Thus W may be an alkylaluminum compound, while the second compound may be a dialkylzinc compound and the third compound may be a borane such as tris(pentafluorophenyl)borane. Such combinations and compounds for W are well known in the art, see for instance U.S. Pat. Nos. 5,955,555 and 5,866,663, both of which are hereby included by reference.

In many instances compounds (XIV) or (XV), if added directly to a polymerization process, may be active polymerization catalysts without the addition of any cocatalysts, or just the addition of a Lewis acid which may form a relatively noncoordinating anion by abstraction of A⁻ or L²⁻ from the complex. In (XIV) L² may be an alkyl group, which is in fact an oligomer or polymer of the olefinic monomer being polymerized, while L¹ may be an open coordination site or L¹ is one of the olefins being polymerized. For example if ethylene is being polymerized, L² may be —(CH$_2$CH$_2$)$_z$D wherein z is a positive integer and D is an anion (which originally was L²) between which ethylene could insert between L² and the transition metal atom M. In effect under these circumstances (XIV) could be thought of as a socalled living polymer. The chemistry of such types of compounds is known, see for instance U.S. Pat. Nos. 5,866,663 and 5,955,555, both of which are hereby included by reference.

In other preferred forms of (II) and (III) the imino nitrogen atoms are substituted in the same manner as other diimino tridentate catalysts, see for instance U.S. Pat. Nos. 5,955,555, 6,103,946, 6,545,108, 6,579,832, 6,559,091, 6,657,026, 6,451,939, 6,455,660, 6,458,739, 6,472,341, 6,451,939, 6,683,187, and 6,710,006, all of which are hereby included by reference.

(III) is made by first synthesizing the corresponding tricyclic diketone

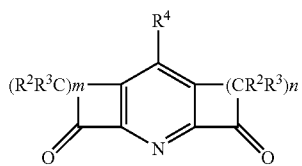

(XII)

wherein m and n are each independently an integer of 2 to 5, each R² and R³ is independently hydrogen, hydrocarbyl, substituted hydrocarbyl or a functional group, and R⁴ is hydrogen, hydrocarbyl substituted hydrocarbyl or a functional group. These diketones can be made by the procedure described in R. P. Thummel, et al., J. Org. Chem., vol. 50, p. 2407-2412 (1985), which is hereby included by reference. Then (XII) can be reacted with the appropriate primary amine(s) to form the diimine (III), as is well known in the art and described in the Examples herein.

Most often the conditions used for olefin polymerization with the present transition metal complexes are similar to those used with other iron and cobalt tridentate complexes which are polymerization catalysts, see for instance U.S. Pat. No. 5,955,555, WO9912981, WO9946302, WO9946303, WO9946304, WO0015646, WO0024788, WO0032641, WO0050470, WO0069869 and WO0069923, all of which are hereby incorporated by reference and describes polymerizations to higher molecular weight polymers. Oligomerizations, especially dimerization and oligomerization of ethylene and other alpha-olefins, to produce alpha-olefins and internal olefins, are described in U.S. Pat. No. 6,063,881, U.S. Pat. No. 6,103,946, WO0055216 and WO0073249, all of which are also incorporated by reference.

The molecular weight of the polymer produced, may if desired, be reduced by using a chain transfer agent such as hydrogen. Conditions for using hydrogen are similar to those found in U.S. Pat. No. 6,252,002, which is hereby included by reference.

Generally speaking the present complexes are effective polymerization catalysts from about −20° C. to about 200° C., preferably about 0° C. to about 150° C. The pressure (if one or more monomers such as ethylene are gaseous) is not critical, atmospheric pressure to 70 MPa being a useful range. Any combination of temperature and pressure may be used. The particular combination of temperature and pressure chosen will reflect many factors, including polymer (or oligomer) yield, type of polymerization process being used, the relative economics of various conditions, etc. A cocatalyst is often added which is an alkylating are hydriding agent. A preferred type of cocatalyst is an alkylaluminum compound, and preferred alkylaluminum compounds are methylaluminoxane, trimethylaluminum, and other trialkylaluminum compounds. Especially preferred alkylaluminum compounds are methylaluminoxane, trimethylaluminum.

The polymerization process may be a batch, semibatch or continuous process, and a continuous process is preferred. The type of process employed may be gas phase, solution, or slurry process, and is dependent somewhat on the product being, produced. These types of processes are well known in the art. For example a solution process may be carried out in one or more continuous stirred tank reactors (CSTR), a slurry process in one or CSTRs or loop reactors, and a gas phase process in one or more fluidized bed reactors and/or loop reactors.

For slurry and gas phase processes it is preferred that the catalyst be on a support such as alumina, magnesium chloride or silica. The catalyst may be attached to the support by any number of known processes. For example a support such as silica may be reacted with an alkylaluminum compound and then with the transition metal complex. Other supportation methods and types of supports, which are useful, are found in World Patent Applications 02/79276 and 02/83751, and U.S. Pat. Nos. 6,313,061, 6,399,535, and 6,184,171, all of which are hereby included by reference. These catalysts may also undergo other treatments known to late transition metal complexes which are polymerization catalysts, see for instance (CL2424) U.S. Patent Application No. 60/505,906 which is all hereby included by reference. In all of these references, when a 2,6-pyridinedicarboxaldehyde diimine or 2,6-diacylpyridine diimine is used, a similar (producing the same type of product) complex as described herein may be used.

A preferred olefin for polymerization is ethylene, more preferably only ethylene. When ethylene is the olefinic monomer, when higher molecular weight polymers are produced they are usually a form of highdensity polyethylene (HDPE), which preferably has a weight average molecular weight (M$_w$) of about 10,000, more preferably about 20,000, Daltons or more. Such a polymer may be made in a gas phase or slurry process. Some of these complexes may also be used to make linear α-olefins (LAOs), in which case a solution process is most commonly used. Types of processes useful for making LAOs are described in U.S. Pat. Nos. 6,534,691, 6,555,723 and World Patent Application 04/026795, all of which are hereby included by reference. In these references, when a 2,6-pyridinedicarboxaldehyde diimine or 2,6-diacylpyridine diimine is used to make LAOs, a similar (producing the same type of product) complex as described herein may be used.

When ethylene is used as a monomer the partial pressure of ethylene in the reactor may, for example, be in the range of about 100 kPa to about 35 MPa, preferably about 300 kPa to about 10 MPa.

The present complexes, whether they are used to make higher molecular weight polymers, LAOs, or intermediate (molecular weight) products, may be used in combination with other "types" of olefin polymerization catalysts to produce useful polymeric products. Such processes, products therefrom and their uses, are described in U.S. Pat. Nos. 6,214,761, 6,297,338, 6,620,897, 6,620,895, 6,555,631, 6,407,188, and 6,586,541, and World Patent Application 03/059511, all of which are hereby included by reference. The "other" types of olefin polymerization catalysts may include the transition metal complexes described herein, for example a complex which produces LAOs may be used in combination with a complex which produces HDPE, as described in these references. In these references, when a 2,6-pyridinedicarboxaldehyde diimine or 2,6-diacylpyridine diimine is used, a similar (producing the same type of product) complex as described herein may be used.

LAOs are useful as monomers and chemical intermediates. Polymers made by the present olefin polymerization catalysts are useful as films and for molding resins.

The diketones used in the Examples, 2,3,7,8-tetrahydro-1H,6H-acridine-4,5-dione and 1,2,6,7-tetrahydro-4-aza-s-indacene-3,5-dione were made by the procedure described in R. P. Thummel, et al., J. Org. Chem., vol. 50, p. 2407-2412 (1985).

In the Examples certain abbreviations are used, and they are:

ΔH$_f$—heat of fusion (measured during the Tm measurement)
GC—gas chromatography
MMAO—modified methylaluminoxane (modified with some isobutyl groups), 7 wt. % in o-xylene, sold as MMAO-3A (from Akzo-Nobel).
Mn—number average molecular weight determined by gel permeation chromatography.
Mw—weight average molecular weight determined by gel permeation chromatography.
Tm—melting point determined by ASTM D3418-82, at a heating rate of 10° C./min with the peak of the melting endotherm is taken as the melting point.

EXAMPLE 1

4,5-Bis-2'-methylphenylimino-1,2,3,4,5,6,7,8-octahydro-acridine (1)

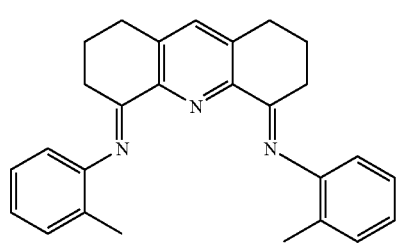

(1)

2,3,7,8-Tetrahydro-1H,6H-acridine-4,5-dione (0.5 g, 2.32 mmol), 0.55 g (5.13 mmol) of o-tolylamine, a few crystals of p-toluenesulfonic acid and 8 ml of ethanol were refluxed for 8 h under argon with stirring. Upon cooling the reaction mixture to ambient temperature, a red precipitate formed. It was filtered off and washed with 10 ml of cold ethanol and dried under 133 Pa (absolute) pressure for 12 h. Yield of (1) was 0.62 g (68%) with an mp of 256° C. $^{13}$C-NMR (CD$_2$Cl$_2$) (selected signals): 161.58 ppm (acyclic C=N). Elemental analysis calculated for C$_{27}$H$_{27}$N$_3$: C, 82.41; H, 6.92; N, 10.68. Found: C, 82.19; H, 6.72; N, 10.50. GC/LS exact mass calculated for C$_{27}$H$_{27}$N$_3$: 393.22; found: 393.22.

EXAMPLE 2

4,5-Bis-2'-methylphenylimino-1,2,3,4,5,6,7,8-octahydro-acridine iron(II)chloride (1a)

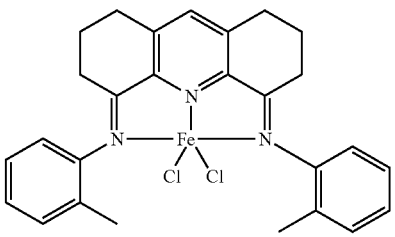

(1a)

(1) (3.12 g, 7.9 mmol), 1.00 g (7.9 mmol) of iron(II)chloride and 100 ml of n-butanol were heated for 30 min at 80° C. A dark precipitate formed and was filtered and washed twice with 40 ml of ethyl ether and dried under 133 Pa (absolute) pressure for 12 h. Yield of (1a) was 2.81 g (68%) as a black powder. Exact mass direct probe calculated for C$_{27}$H$_{27}$Cl$_2$FeN$_3$ was 519.09. Found exact mass with isotopic pattern: m/e: 519.09 (100.0%), 521.09 (62.7%), 520.10 (29.3%), 522.09 (20.8%), 523.09 (10.7%), 517.09 (6.2%), 521.10 (5.1%), 520.09 (4.5%), 524.09 (3.3%), 523.10 (2.8%), 518.10 (1.9%). Elemental analysis calculated for C$_{27}$H$_{27}$C$_{12}$FeN$_3$: C, 62.33; H, 5.23; N, 8.08. Found: C, 62.42; H, 4.86; N, 7.82.

Experiment 1

4-tert-Butylphenyl boronic acid

A solution of para-tert-butylphenyl magnesium bromide prepared from 52 ml of para-tert-butylphenyl bromide and 8.0 g of the magnesium turnings in 250 ml of diethyl ether was added to 81 ml of tri-n-butyl borate in 250 ml of diethyl ether at −80° C. with stirring under argon. The reaction mixture was allowed to warm to ambient temperature, and was poured into 150 ml of 10% sulfuric acid in water. The organic phase was extracted twice by 100 ml of diethyl ether. The solvent and n-butanol were removed under vacuum. The viscous residue was recrystallized from boiling water. Yield of 4-tert-butylphenyl boronic acid was 10% as white crystals with mp. 202-203° C.

Experiment 2

2,6-Di-(para-tert-butylphenyl)aniline 4-tert-Butylphenyl boronic acid (11.7 g), 10.9 g of 2,6-dibromophenylamine, 1.36 g of Pd$_2$(dba)$_3$.CHCl$_3$, and 2.75 g of Ph$_3$P were charged into a 0.5 L round bottom flask containing 50 ml of benzene under argon. Then a solution of 27 g of Na$_2$CO$_3$ in 130 ml of water was added to the flask in one portion. The reaction mixture was refluxed for 120 h. The organic phase was separated and purified by chromatography on silica gel with an eluent of petroleum ether/diethyl ether (20:1), collecting the beginning of the eluate ($R_f$=0.9-1). Yield of 2,6-di-(para-tert-butylphenyl)aniline was 60-70% with mp. 106° C.

EXAMPLE 3

4,5-bis[2,6-di-(4-tert-butylphenyl)phenylimino]-1,2,3,4,5,6,7,8-octahydroacridine (2)

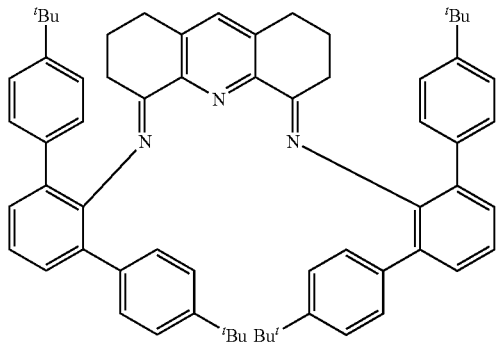

(2)

2,6-Di-(para-tert-butylphenyl)aniline (3.75 g), 1.075 g of 2,3,7,8-tetrahydro-1H,6H-acridine-4,5-dione, a few crystals of p-toluene sulfonic acid and 50 ml of toluene were refluxed under argon with a water separator. The progress of the reaction was determined by TLC experiments. The reaction mixture was purified by chromatography on silica gel with eluent petroleum ether/diethyl ether (20:1), and collecting the initial eluate. The yield of (2) was 2.5 g.

EXAMPLE 4

[4,5-bis[2,6-di-(4-tert-butylphenyl)phenylimino]-1,2,3,4,5,6,7,8-octahydroacridine]iron(II)chloride (2a)

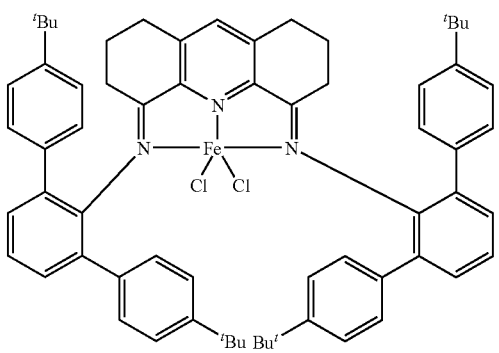

(2a)

A solution of 0.56 g of $FeCl_2.4H_2O$ in 10 ml of MeOH was added in the solution of 2.5 g of (2) in 50 ml of benzene. The resulted reaction mixture was refluxed under argon with removing azeotrope of methanol/benzene. The reaction mixture was cooled to ambient temperature. The formed precipitate was filtered and washed twice by hot benzene and dried in vacuum. The yield of (2a) was 1.0 g.

EXAMPLE 5

[4,5-bis[2,6-dimethylphenylimino]-1,2,3,4,5,6,7,8-octahydroacridine]iron(II)chloride (3a)

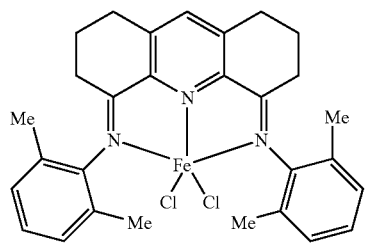

(3a)

(3a) was synthesized by methods similar to those in Examples 3 and 4: 2,6-dimethylaniline was condensed with 2,3,7,8-tetrahydro-1H,6H-acridine-4,5-dione to yield 4,5-bis[2,6-dimethylphenylimino]-1,2,3,4,5,6,7,8-octahydroacridine (3). The complexation of (3) with $FeCl_2.4H_2O$ was carried out with azeotropic removal of methanol in benzene. The structure of final complex was proved by X-ray analysis.

EXAMPLE 6

[4,5-Bis[2,6-di-iso-propylphenylimino]-1,2,3,4,5,6,7,8-octahydroacridine]iron(II)chloride (4a)

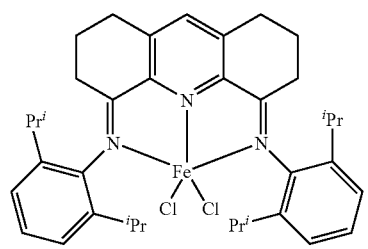

(4a)

(4a) was synthesized by methods similar to those in Examples 3 and 4:: 2,6-di-iso-propylaniline was condensed with 2,3,7,8-tetrahydro-1H,6H-acridine-4,5-dione to yield 4,5-bis[2,6-di-iso-propylphenylimino]-1,2,3,4,5,6,7,8-octahydroacridine (4). The complexation of (4) with $FeCl_2.4H_2O$ was carried out with azeotropic removal of methanol in benzene. The structure of the final complex was proved by direct probe GC. Exact mass direct probe calculated for $C_{37}H_{47}Cl_2FeN_3$: 659.25. Found: 659.25.

EXAMPLE 7

[4,5-Bis[3,5-ditrifluoromethylphenylimino]-1,2,3,4,5,6,7,8-octahydroacridine]iron(II)chloride (5a)

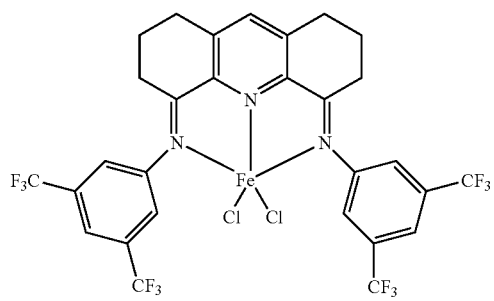

(5a) was synthesized by methods similar to those in Examples 3 and 4: 3,5-bis-trifluoromethylaniline was condensed with 2,3,7,8-tetrahydro-1H,6H-acridine-4,5-dione to yield 4,5-bis[3,5-bistrifluoromethylphenylimino]-1,2,3,4,5,6,7,8-octahydroacridine (5). The complexation of (5) with $FeCl_2.4H_2O$ was carried out with azeotropic removal of methanol in benzene. The structure of the final complex was proved by direct probe GC. Exact mass direct probe calculated for $C_{29}H_{19}Cl_2F_{12}FeN_3$: 763.01. Found: 763.01.

EXAMPLE 8

[4,5-Bis[2,6-di-phenylphenylimino]-1,2,3,4,5,6,7,8-octahydroacridine]iron(II)chloride (6a)

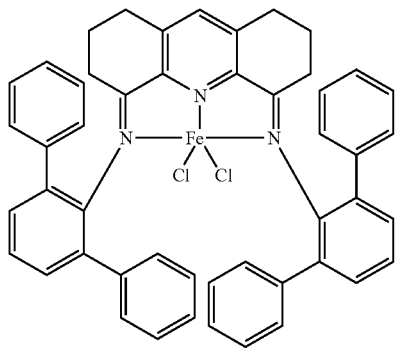

(6a) was synthesized by methods similar to those in Examples 3 and 4: 2,6-diphenylaniline was condensed with 2,3,7,8-tetrahydro-1H,6H-acridine-4,5-dione to yield 4,5-bis[2,6-diphenylphenylimino]-1,2,3,4,5,6,7,8-octahydroacridine (6). Complexation of (6) with $FeCl_2.4H_2O$ was carried out with azeotropic removal of methanol in benzene. The structure of final complex was proved by direct probe GC. Exact mass direct probe calculated for $C_{49}H_{39}Cl_2FeN3$: 795.19. Found: 795.19.

EXAMPLE 9

[4,5-Bis[2-phenylphenylimino]-1,2,3,4,5,6,7,8-octahydroacridine]iron(II)chloride (7a)

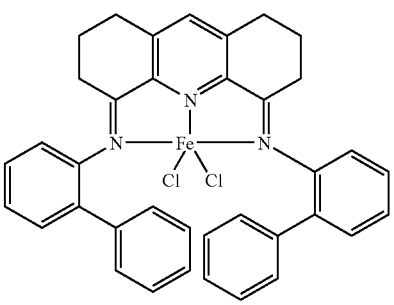

(7a) was synthesized by methods similar to those in Examples 3 and 4: 2-phenylaniline was condensed with 2,3,7,8-tetrahydro-1H,6H-acridine-4,5-dione to yield 4,5-bis(2-phenylphenylimino)-1,2,3,4,5,6,7,8-octahydroacridine (7). The complexation of (7) with $FeCl_2.4H_2O$ was carried out with azeotropic removal of methanol in benzene. The structure of the final complex was proved by direct probe GC. Exact mass direct probe calculated for $C_{37}H_{31}Cl_2FeN_3$: 643.12. Found: 643.12.

EXAMPLE 10

[Alpha, alpha-bis[2-biphenylimino]-2,3:5,6-bis(trimethylene)pyridine]iron(II)chloride (8a)

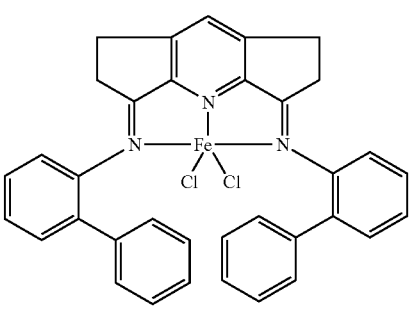

(8a) was synthesized by methods similar to those in Examples 3 and 4: 2-phenylaniline was condensed with 1,2,6,7-tetrahydro-4-aza-sindacene-3,5-dione to yield alpha,alpha-bis[2-biphenylimino]-2.3:5,6-bis(trimethylene)pyridine (8). The complexation of (8) with $FeCl_2.4H_2O$ was carried out with azeotropic removal of methanol in benzene. The structure of the final complex was proved by direct probe GC. Exact mass direct probe calculated for $C_{35}H_{27}Cl_2FeN_3$: 615.09. Found: 615.09.

EXAMPLES 11-14

Ethylene was polymerized in a stirred 500 ml Autoclave Engineers (Erie, Pa. 16509 USA) Zipperclave® autoclave. The autoclave was equipped with two 25 ml Swagelok® addition tubes that could be pressureized and then vented (emptied) into the autoclave. One of the tubes was loaded with 2 ml of MMAO, and the other tube was loaded with a slurry of the iron complex in 50 ml of toluene.

The autoclave was rinsed with hexane, closed and pressure tested and purged with $N_2$. The autoclave was heated to 100° C. and purged with $N_2$ (pressure about 140 kPa) for 1 h, and then vented. The autoclave pressurized to 690 kPa with $N_2$ and was then cooled to 60° C., the polymerization temperature. Then 250 ml of cyclohexane was added, and the stirrer was set at 1000 rpm. The MMAO cocatalyst was then loaded into the autoclave using $N_2$ pressure and the autoclave pressured to 2.07 MPa with ethylene. The iron complex slurried in 50 ml of toluene was then pressurized into the catalyst feed tank. The catalyst slurry was then pumped into the autoclave for 3 min and then stopped. The autoclave was maintained at 2.07 MPa of ethylene pressure and 60° C. for 1 h while the polymerization proceeded.

After 1 h the ethylene flow was stopped and the reactor was cooled to room temperature. The stirrer was stopped and the reactor was vented to atmospheric pressure. The reactor was opened and the contents were weighed and then filtered through a 600 ml coarse glass frit Buchner funnel. The polymer was dried overnight at room temperature under vacuum (60 kPa absolute) with a slight $N_2$ purge. After drying the polymer was weighed. Details of the polymerization conditions and polyethylenes obtained are given in Table 1.

TABLE 1

| Ex. | Complex (mg) | Polymer, g | Catalyst Slurry Feed Rate ml/min | Polymer $\Delta H_f$, J/g | Tm, °C. | Mn | Mw |
|---|---|---|---|---|---|---|---|
| 11 | 2a (1.856) | 64.6 | 5.33 | | | | |
| 12 | 2a (0.375) | 13.0 | 1.79 | 151.0 | 129.0 | 325 | 58123 |
| 13 | 6a (1.484) | 26.7 | 4.67 | 126.7 | 125.9 | | |
| 14 | 6a (0.375) | 1.7 | 5.45 | 15.6 | 120.8 | | |

In at least some examples the relatively low melting point was probably caused by the relatively molecular weight of the polyethylene formed.

EXAMPLE 15

[5-(2-Trifluoromethylphenylimino)-2,3,5,6,7,8-hexahydro-1H-acridin-4-ylidene]-(2-trifluorbmethylphenyl)-amine (10)

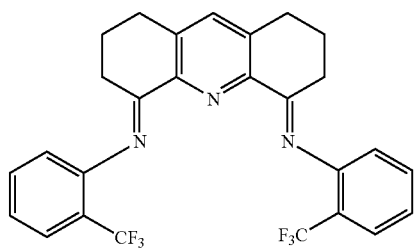

(10)

A mixture of 2.5 g (11.63 mmol) of 2,3,7,8-tetrahydro-1H, 6H-acridine-4,5-dione, 4.49 g (27.88 mmol) of 2-aminobenzotrifluoride and 0.03 g of toluene-4-sulfonic acid in 40 ml of benzene was stirred under reflux with the azeotropic distillation of water for 4 h. The solvent was removed in vacuo. Forty ml of hexane was added to the residue and the mixture was stirred for 0.5 h. The dark-yellow precipitate formed was filtered off, washed carefully with hexane and dried at 13 Pa (absolute) for 2 h. The yield of (10) was 3.25 g (55%), mp. 162-164° C.

IR (Nujol, v, cm$^{-1}$): 473 w, 521 w, 598 w, 621 w, 653 m, 691 w, 740 w, 757 s, 816 w, 912 w, 947 w, 987 w, 1019 m, 1034 s, 1060 m, 1103 s, 1125 s, 1169 s, 1214 m, 1240 m, 1277 m, 1294 m, 1318 s, 1377 w (Nujol), 1423 s; 1435 s, 1461 s (Nujol), 1481 m, 1520 s, 1583 s, 1610 s, 1646 m (C=N), 2855 br. s (Nujol), 2925 br.s (Nujol), 3050 w (C—H$_{ar}$), 3329 w (N—H), 3400 m (N—H). MS, m/z (1%): M$^+$·502(6), 501 (19), 500(3), 480(4), 460(5), 129(20), 111(38), 109(20), 83(100)

EXAMPLE 16

[5-(2-Trifluoromethylphenylimino)-2,3,5,6,7,8-hexahydro-1H-acridin-4-ylidene]-(2-trifluoromethylphenyl)-amine iron(II)chloride (10a)

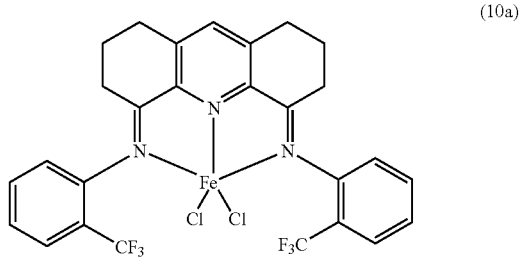

(10a)

(10a) was synthesized by methods similar to those in Examples 3 and 4 from 3.25 g (6.48 mmol) of [5-(2-trifluoromethylphenylimino)-2,3,5,6,7,8-hexahydro-1H-acridin-4-ylidene]-(2-trifluoromethylphenyl)amine and 0.84 g (6.61 mmol) iron (II) chloride. The yield of (10a) was 3.97 g (97%) as a black powder.

IR (Nujol, v, cm$^{-1}$): 653 m, 687 w, 721 w, 764 s, 789 m, 836 w, 925 w, 937 w, 992 w, 1035 s, 1057 s, 1120 br.s., 1171 s, 1208 m, 1242 m, 1270 m, 1320 br.s., 1348 m, 1377 m (Nujol), 1456 br.s (Nujol), 1491 m, 1582 s, 1604 s, 1632 m (C=N), 1670 w, 2854 br. s (Nujol), 2922 br.s (Nujol), 3384 br. w (N—H). MS m/z (1%): M+.−629 (0.9) 627 (1.4), 501(44), 412(16), 220(20), 198(40), 145(100), 114(16), 95(40), 79(47), 69(23) 57(25), 55(31), 42(27), 36(24)

EXAMPLE 17

[5-(2-Trifluoromethylimino)-1,5,6,7-tetrahydro-2H-4-aza-s-indacen-3-ylidene]-(2-trifluoromethylphenyl)-amine (11)

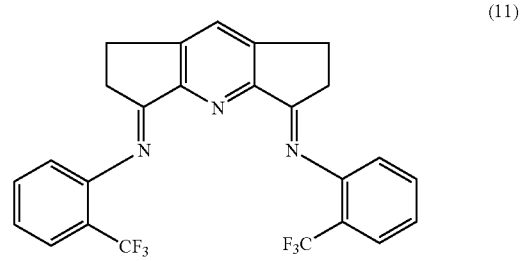

(11)

A mixture of 4 g (21.39 mmol) of 1,2,6,7-tetrahydro-4-azasindacene-3,5-dione, 10.33 g (64.16 mmol) of 2-aminobenzotrifluoride and 0.05 g of toluene-4-sulfonic acid in 100 ml of toluene was stirred under reflux with the azeotropic distillation of water for 10 h. The black precipitate formed was filtered off, washed by toluene and benzene and dried at 13 Pa (absolute) for 2 h. The yield of (11) was 6.50 g (64%), mp.>350° C.

IR (Nujol, ν, cm$^{-1}$): 653 w, 755 m, 850 w, 881 w, 944 w, 1036 s, 1058 m, 1117 br. s, 1167 s, 1290 s, 1321 s, 1379 s (Nujol), 1464 s (Nujol), 1549 m, 1591 br. s, 1719 w, 2854 br.s (Nujol), 2924 br.s (Nujol), 3398 brew (N—H). MS, m/z (1%): M$^{+}$ 473 (1.5), 161(100), 141(86), 113(82)

EXAMPLE 18

[5-(2-Trifluoromethylphenylimino)-1,5,6,7-tetrahydro-2H-4-aza-s-indacen-3-ylidene]-(2-trifluoromethylphenyl)-amine Iron(II)chloride (11a)

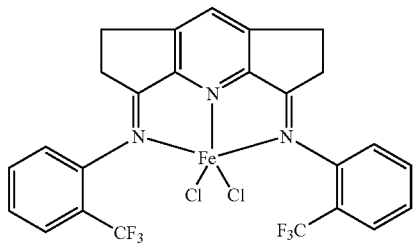

(11a)

(11a) was synthesized by methods similar to those in Examples 3 and 4 from 5.00 g (10.57 mmol) of (11) and 1.38 g (10.86 mmol) iron (II) chloride. The yield of (11a) was 6.20 g (97%) as a black powder.

EXAMPLE 19

[5-(2,6-Di-fluorophenylimino)-2,3,5,6,7,8-hexahydro-1H-acridin-4-ylidene]-(2,5-di-fluorophenyl)-amine (12)

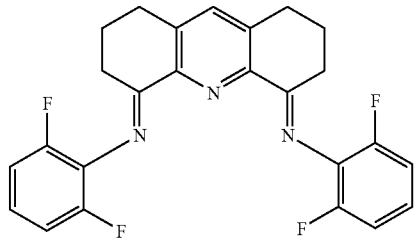

(12)

A mixture of 3.05 g (14.1 mmol) of 2,3,7,8-tetrahydro-1H, 6H-acridine-4,5-dione, 4.0 ml (4.80 g, 37.2 mmol) of 2,6-difluoroaniline and 0.03 g of toluene-4-sulfonic acid in 40 ml of benzene was stirred under reflux with the azeotropic distillation of water for 8 h. The solvent was removed in vacuum and 40 ml of cold hexane was added to the residue. and the mixture was stirred for 0.5 h. The dark-red precipitate formed was filtered off, washed carefully with hexane and dried at 13 pa (absolute) for 2 h. The yield of (12) was 4.8 g (77%) with mp. 145-150° C.

IR (Nujol, ν, cm$^{-1}$): 682 m, 720 w, 764 w, 792 w, 847 w, 921 w, 979 w, 1002 s, 1034 w, 1113 m, 1167 m, 1213 s, 1237 m, 1272 w, 1294 w, 1324 w, 1377 w (Nujol), 1466 s (Nujol), 1509 m, 1591 m, 1647 m (C=N), 2855 br. s (Nujol), 2925 br.s (Nujol), 3343 w (N—H). MS, m/z (1%): M 437(1.2)

EXAMPLE 20

[5-(2,6-Di-fluorophenylimino)-2,3,5,6,7,8-hexahydro-1H-acridin-4-ylidene]-(2,5-di-fluorophenyl)-amine (12a)

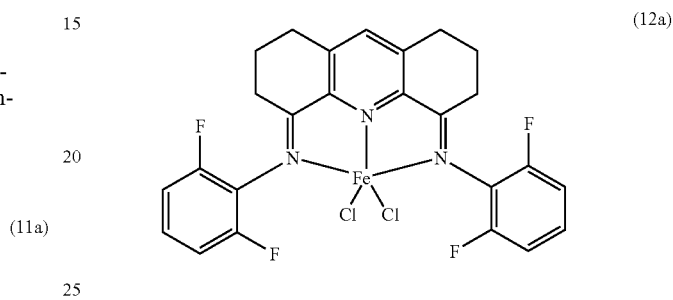

(12a)

(12a) was synthesized by methods similar to those in Examples 3 and 4 from 6.08 g. (13.91 mmol) of (12) and 1.80 g (14.17 mmol) of iron (II) chloride. The yield of (12a) was 7.04 g (89%) as a black powder.

IR (Nujol, ν, cm$^{-1}$): 666 m, 693 w, 713 w, 767 m, 794 w, 821 w, 923 w, 1008 s, 1062 w, 1112 m, 1166 m, 1240 s, 1282 m, 1326 w, 1349 w, 1377 s (Nujol), 1471 s (Nujol), 1590 s, 1620 m, 1671 m (C=N), 2854 br. s (Nujol), 2924 br.s (Nujol), 3344 w (N—H). MS m/z(1%): 527(1.2) и 525(2.3) (M$^{+}$−2F).

EXAMPLE 21

[5-(3,5-Di-tert-Butyl-phenylimino)-2,3,5,6,7,8-hexahydro-1H-acridin-4-ylidene]-(3,5-di-tert-butyl-phenyl)-amine (13)

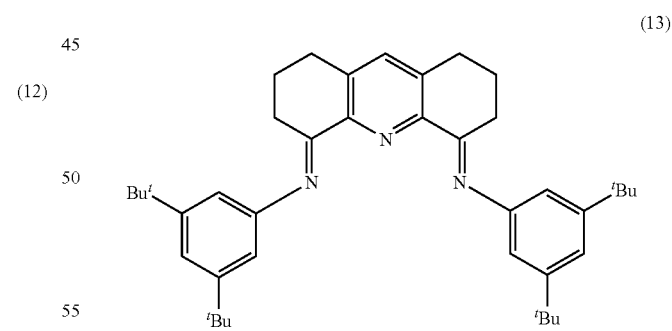

(13)

A mixture of 1.72 g (8 mmol) of 2,3,7,8-tetrahydro-1H, 6H-acridine-4,5-dione, 3.31 g (16.2 mmol) of 3,5-di-tert-butylaniline and 0.03 g of toluene-4-sulfonic acid in 40 ml of benzene was stirred under reflux with the azeotropic distillation of water for 4 h. The solvent was removed in vacuum, and 40 ml of cold MeOH was added to the residue and the mixture was stirred for 0.5 h. The dark-orange precipitate formed was filtered off, washed carefully with MeOH and dried at 13 Pa (absolute) for 2 h. The yield of (13) was 3.8 g (76%) with mp. 129-132° C.

IR (Nujol, ν, cm$^{-1}$): 665 w, 709 m, 801 w, 853 w, 900 w, 962 w, 1020 m, 1130 m, 1166 m, 1204 s, 1247 s, 1327 s, 1362 s, 1377 w (Nujol), 1455 s, (Nujol), 1528 s, 1598 s, 1695 m (C=N), 2855 br. s (Nujol), 2923 br.s (Nujol), 3356 w (N—H). MS, m/z (1%): M$^+$590(50), 589(100), 588(27), 533 (18), 532(19), 385(22), 83(20), 57(43).

EXAMPLE 22

[5-(3,5-Di-tert-Butyl-phenylimino)-2,3,5,6,7,8-hexahydro-1H-acridin-4-ylidene]-(3,5-di-tert-butyl-phenyl)-amine Iron(II)Chloride (13a)

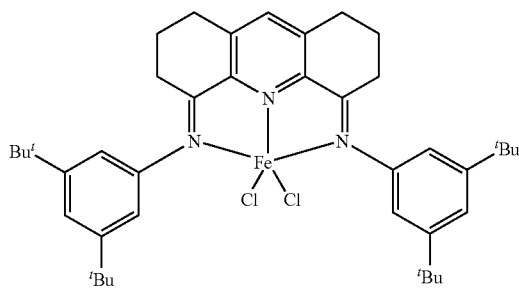

(13a)

(13a) was synthesized by methods similar to those in Examples 3 and 4 from 4.27 g. (7.24 mmol) of (13) and 0.94 g (7.40 mmol) iron (II) chloride. The yield of (13a) was 5.04 g (96%) as a black powder.

IR (Nujol, ν, cm$^{-1}$): 658 w, 709 m, 876 w, 899 w, 924 w, 1034 s, 1168 m, 1203 m, 1247 s, 1308 m, 1364 s, 1377 s (Nujol), 1395 m, 1460 s (Nujol), 1596 m, 1677 m (C=N), 1719 w, 2856 br. s (Nujol), 2926 br.s (Nujol), 3347 w (N—H). MS m/z(1%): M$^+$717 (71), 715 (100), 680(26), 623(22), 590(28), 589(82), 386(30), 218(30), 205(40), 204(40), 133 (28), 57(18).

EXAMPLE 23

[5-(3,5-Di-tert-butyl-phenylimino)-1,5,6,7-tetrahydro-2H-4-aza-s-indacen-3-ylidene]-(3,5-di-tert-butyl-phenyl)-amine (14)

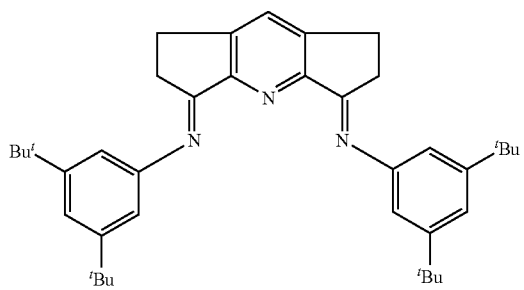

(14)

A mixture of 2.04 g (11 mmol) of 1,2,6,7-tetrahydro-4-aza-sindacene-3,5-dione, 4.8 g (23.4 mmol) of 3,5-di-tert-butylaniline and 0.03 g of toluene-4-sulfonic acid in 40 ml of benzene was stirred under reflux with the azeotropic distillation of water for 4 h. The solvent was removed in vacuum, and 40 ml of MeOH was added to the residue and the mixture was stirred for 0.5 h. The dark-brown precipitate formed was filtered off, washed carefully with cold MeOH and dried at 13 Pa (absolute) for 2 h. The yield of (14) was 3.27 g (52.7%) with mp. 177-183° C.

IR (Nujol, ν, cm$^{-1}$): 707 s, 855 m, 900 w, 954 w, 1000 w, 1028 m, 1134 s, 1164 s, 1203 s, 1247 s, 1310 s, 1363 s, 1377 w (Nujol), 1463 s (Nujol), 1595 s, 1718 m (C=N), 2855 br. s (Nujol), 2925 br.s (Nujol), 3369 w (N—H). MS, m/z (1%): M$^+$-561 (0.5), 206(30), 205(96), 191(25), 190(100), 163 (40), 134(78), 106(21), 57(35).

EXAMPLE 24

[5-(3,5-Di-tert-butyl-phenylimino)-1,5,6,7-tetrahydro-2H-4-aza-s-indacen-3-ylidene]-(3,5-di-tert-butyl-phenyl)-amine (14a)

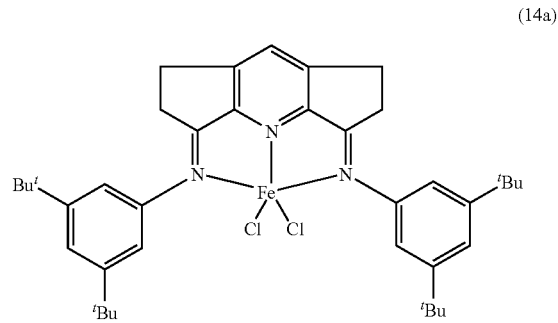

(14a)

(14a) was synthesized by methods similar to those in Examples 3 and 4 from 4.90 g. (8.31 mmol) of (14) and 1.10 g (8.65 mmol) iron (II) chloride. The yield of (14a) was 5.42 g (91%) as a black powder.

IR (Nujol, ν, cm$^{-1}$): 707 w, 791 w, 874 w, 900 w, 947 w, 1170 m, 1247 m, 1311 m, 1364 s, 1378 s (Nujol), 1460 s (Nujol), 1594 s, 1720 m (C=N), 2855 br. s (Nujol), 2923 br.s (Nujol), 3345 w (N—H). Calculated (%) C, 68.03; H, 7.47; Cl, 10.30; Fe, 8.11; N, 6.10 for $C_{39}H_{51}Cl_2FeN_3$. Found (%) C, 68.3; H, 7.12; Cl, 10.79; N, 5.90.

EXAMPLES 25-33

In these examples certain of the iron complexes were used to pre-pares linear α-olefins. The apparatus used was a jacketed 1 l Autoclave Engineers Zipper autoclave equipped with a dual-blade finned variablespeed agitator. It was heated by feeding a mixture of steam and cold water to the jacket. Catalyst and cocatalyst were fed from addition tubes below the liquid surface through dip tubes. Ethylene was fed through a Research Control Valve into the headspace. The ethylene flow rate was monitored using a mass flow meter. A pressure transducer, connected directly to the reactor head, provided a reactor pressure reading and provided input for the operation of the ethylene feed control valve. A thermocouple for temperature measurement was inserted through the head of the reactor into the liquor. The autoclave had a dump valve to allow for draining it without opening the unit.

In a dry box, the desired volume of catalyst and cocatalyst (2.00 ml MMAO-3A from Akzo Nobel, 7.0 wt. % solution in o-xylene) solutions were into separate addition tubes. In separate bulbs above these charges, the desired volume of rinse solvent was added. Tel ml of o-xylene was used to rinse each tube. The addition tubes were attached to ports on the 1-liter autoclave, while purging the connections with nitrogen. The autoclave was depressurized and charged with 600 ml of o-xylene. The agitator was turned on to 1000 rpm and the heater controller turned on to achieve the desired batch temperature. When the batch temperature was stable, any residual nitrogen was vented. Opened the feed line to ethylene. Charged the cocatalyst by flowing ethylene through its addition tube to achieve about 2.1 MPa gauge in the autoclave. The pressure controller was set to 4.83 MPa gauge and activate it. With the ethylene pressure at 4.83 MPa and the temperature at the desired value, the catalyst solution was pushed into the reactor using nitrogen. The run was allowed to continue for 30 min or until no further ethylene uptake was detected by the mass flow meter. A high-pressure sampler was attached to the autoclave drain port. The agitator and ethylene feed were turned off and the valves positioned to first fill the purge capsule and then the sampling capsule. The agitator was restarted and the reactor was cooled to <60° C. and then the contents were drained into a 1 l screw cap bottle. A high-pressure sample was vented into a gas sampling bag to analyze for ethylene and butene content via GC. The liquid fraction was injected into a gas chromatograph using a standard addition method to quantify the amount of soluble LAO present. The autoclave liquor was allowed to cool to room temperature and then filtered enough of the liquor to recover a solids sample for determination of the weight fraction of insoluble LAO present.

Catalysts are made up in the same solvent used in the reactor at a concentration of 0.01 to 0.009 g/100 ml. When μl catalyst is specified, it means the volume of the catalyst "solution" added. Most do not go completely into solution so the catalyst solution is stirred while withdrawing the desired volume for each run.

At the end of a run, the liquor was allowed to reach room temperature and then a know weight of that liquor, with the solids well suspended, and was filtered to determine the percent solids.

The weight fractions of the various α-olefins produced was determined using gas chromatography with internal standards method. The K factor was then calculated using standard methods for this constant.

The yields linear α-olefins (LAOs) is in Table 2. There is a separate column for insoluble (% solids) and soluble LAOs. They are given as the weight percents of the overall liquor removed from the reactor.

TABLE 2

| Ex | Catalyst | Temp, ° C. | μmoles Catalyst | Wt % Solid LAO | K value | Wt % Soluble LAO |
|---|---|---|---|---|---|---|
| 25 | 1A | 80 | 0.75 | — | 0.51 | — |
| 26 | 1A | 80 | 0.93 | 0.08 | 0.48 | — |
| 27 | 1A | 120 | 0.93 | 0.06 | 0 | — |
| 28 | 1A | 50 | 0.37 | 0.17 | 0.58 | — |
| 29 | 1A | 30 | 0.37 | 0.61 | 0.7 | 2.76 |
| 30 | 10A | 70 | 0.59 | 0.552 | 0.77 | 0.13 |
| 31 | 11A | 70 | 0.61 | 0.118 | 0.66 | 2.48 |
| 32 | 12A | 70 | 0.69 | 0.139 | 0.6 | 6.39 |
| 33 | 13A | 70 | 0.52 | 0.183 | 0.69 | 2.57 |

What is claimed is:

1. A process for the polymerization or oligomerization of olefins, comprising, contacting one or more olefins of the formula:

$$R^1CH=CH_2 \quad (I),$$

with an iron or cobalt complex of a diimine of a diketone of the formula:

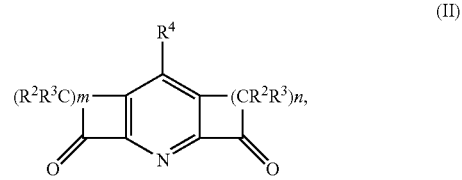

wherein:
(i) $R^1$ is hydrogen or n-alkyl;
(ii) m and n are each independently an integer of 1 to 5;
(iii) each $R^2$ and $R^3$ is independently hydrogen, hydrocarbyl, substituted hydrocarbyl, or a functional group; and
(iv) $R^4$ is hydrogen, hydrocarbyl, substituted hydrocarbyl, or a functional group.

2. The process as recited in claim 1, wherein m and n are both 2 or 3, $R^4$ is hydrogen, and wherein $R^2$ and $R^3$ are hydrogen.

3. The process as recited in claim 1, wherein (II) has the formula:

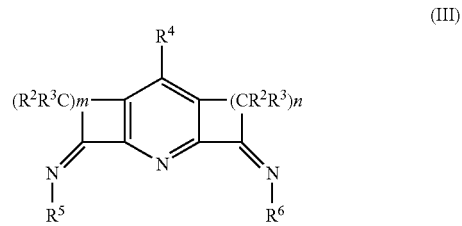

wherein $R^5$ and $R^6$ are hydrocarbyl or substituted hydrocarbyl.

4. The process as recited in claim 3, wherein $R_5$ and $R^6$ are each independently aryl or substituted aryl.

5. The process as recited in claim 4, wherein $R^5$ and $R^6$ are each independently phenyl, substituted phenyl, 1-pyrrolyl or substituted 1-pyrrolyl.

6. The process as recited in claim 1, wherein said olefin comprises ethylene.

7. The process as recited in claim 6, wherein the olefin is ethylene only.

8. The process as recited in claim 1, wherein a polymer having a weight average molecular weight of about 10,000 Daltons or more is produced.

9. The process as recited in claim 1, wherein linear alpha-olefins are produced.

10. The process as recited in claim 3, wherein $R^5$ and $R^6$ are each independently aryl or substituted aryl, m and n are both 2 or 3, $R^4$ is hydrogen, every $R^2$ and $R^3$ is hydrogen, and said olefin comprises ethylene, and said complex is an iron complex.

* * * * *

UNITED STATES PATENT AND TRADEMARK OFFICE
CERTIFICATE OF CORRECTION

PATENT NO. : 7,683,149 B2
APPLICATION NO. : 12/218030
DATED : March 23, 2010
INVENTOR(S) : Alex Sergey Ionkin and Lynda Kaye Johnson It is certified that error appears in the above-identified patent and that said Letters Patent is hereby corrected as shown below:

In Column 26, Claim 4, Line 45 please change "wherein $R_5$" to read -- wherein $R^5$ --.

Signed and Sealed this

Fourteenth Day of December, 2010

David J. Kappos
*Director of the United States Patent and Trademark Office*